United States Patent [19]

Kawa et al.

[11] Patent Number: 5,711,899
[45] Date of Patent: Jan. 27, 1998

[54] FREE FLOWING PEARLESCENT CONCENTRATE

[75] Inventors: Rolf Kawa, Monheim; Achim Ansmann, Erkrath; Angelika Jung, Monheim-Baumberg, all of Germany

[73] Assignee: Henkel Kommanditgesellschaft auf Aktien, Duesseldorf, Germany

[21] Appl. No.: 699,174

[22] Filed: Aug. 19, 1996

Related U.S. Application Data

[63] Continuation of Ser. No. 679,076, filed as PCT/EP89/01542 Dec. 14, 1989, abandoned.

[30] Foreign Application Priority Data

Dec. 23, 1988 [DE] Germany .......................... 38 43 572.1

[51] Int. Cl.$^6$ .............................. A61K 7/08; B01J 13/00; C11D 1/90; C11D 17/00
[52] U.S. Cl. .......................... 252/311; 252/312; 252/314; 424/70.19; 424/70.21; 424/70.31; 510/130; 510/159; 510/416
[58] Field of Search ...................... 252/311, 312, 252/314; 514/941, 943; 424/70.19, 70.21, 70.31; 510/416

[56] References Cited

U.S. PATENT DOCUMENTS

| | | | |
|---|---|---|---|
| 4,137,191 | 1/1979 | Lohr | 252/DIG. 13 |
| 4,486,334 | 12/1984 | Horiuchi et al. | 252/312 |
| 4,654,163 | 3/1987 | Quack et al. | 252/312 |
| 4,654,207 | 3/1987 | Preston | 424/70 |
| 4,777,038 | 10/1988 | Scheuffgen | 424/70 |
| 4,824,594 | 4/1989 | Hoeffkes et al. | 252/DIG. 13 |
| 5,017,305 | 5/1991 | Hoeffkes et al. | 252/311 |

FOREIGN PATENT DOCUMENTS

| 1137807 | 6/1986 | Japan | 424/70 |
|---|---|---|---|

OTHER PUBLICATIONS

*Kirk–Othmer Encyclopedia of Chemical Technology*, 169–70 (3d ed., New York, John Wiley & Sons, 1979).

*The Merck Index*, 876–77 (8th ed., Rahway, NJ, Merck & Co., Inc., 1968).

*Primary Examiner*—Richard D. Lovering
*Attorney, Agent, or Firm*—Ernest E. Szoke; Wayne C. Jaeschke; Real J. Grandmaison

[57] ABSTRACT

Pearlescent concentrates containing 15 to 40% by weight pearlescing components may be formulated in the form of a free-flowing aqueous dispersion providing the dispersion simultaneously contains 5 to 55% by weight nonionic, ampholytic and/or zwitterionic surfactants and 0.1 to 5% by weight low molecular weight polyhydric alcohols.

10 Claims, No Drawings

5,711,899

FREE FLOWING PEARLESCENT CONCENTRATE

This application is a continuation application of Ser. No. 07/679,076 filed on Jun. 21, 1991, now abandoned which is 371 of PCT/EP89/01542, filed Dec. 14, 1989.

BACKGROUND OF THE INVENTION

1. Field of the Invention

This invention relates to a pearlescent concentrate in the form of a free-flowing or pumpable, aqueous dispersion containing 15 to 40% by weight pearlescing components.

2. Statement of Related Art

Aqueous preparations of surfactants and cosmetic preparations can be given a pearlescent, aesthetically attractive appearance by incorporation of substances which, after cooling, precipitate in the form of fine nacreous-looking crystals and remain dispersed in the preparations. Suitable so-called pearlescers are, for example, the monoesters and diesters of ethylene glycol, propylene glycol and oligomeric alkylene glycols of this type or glycerol with $C_{16-22}$ fatty acids, fatty acids and also monoalkanolamides of fatty acids with $C_2$ or $C_3$ alkanolamines.

It is also known that the pearlescers mentioned form stable dispersions in water or in aqueous surfactant solutions and that the concentrated pearlescent dispersions obtained in this way can be added without heating to the preparations to be given a pearlescent appearance, so that there is no longer any need for the heating and cooling otherwise necessary for incorporation to form the pearlescent crystals.

Pearlescent concentrates based on the pearlescers mentioned above are known, for example, from DE-A-16 69 152, from JP-56/71021 (Chem. Abstr. 95/156360), from DE-A-34 11 328 and DE-A-35 19 081. The pearlescent concentrates known from DE-A-16 69 152 contain anionic surfactants to stabilize the dispersion in its liquid state. However, the presence of ionic surfactants is undesirable in many applications of such pearlescent concentrates because incompatibility with formulation constituents of opposite ionicity can arise and can adversely affect the stability of the dispersion.

In addition, the pearlescent concentrates known from these publications contain fatty acid monoalkanolamides or dialkanolamides as part of the pearlescers. However, alkanolamines and derivatives thereof have recently been suspected of participating in the formation of nitrosoamines, with the result that efforts are being made to manage without alkanolamines and alkanolamine derivatives in the formulation of cosmetic preparations.

However, omission of the fatty acid alkanolamides from the known pearlescent concentrates leads to a distinct reduction in the pearlescent properties. Accordingly, it was proposed in Applicants' German patent application 37 24 547.3 to use pearlescent concentrates containing substantially linear, saturated fatty acids as the pearlescing component. However, distinctly higher concentrations of pearlescing components are required to obtain satisfactory pearlescence in the end product.

The pearlescent concentrates known from JP-56/71021 are attended by the disadvantage that they are not free-flowing and do not form stable, free-flowing dispersions on corresponding dilution with water. This makes the concentrates very difficult to handle and process on an industrial scale.

DESCRIPTION OF THE INVENTION

Objects of the Invention

However, there is still a need for pearlescent concentrates having high concentrations of pearlescing components for the same stability which are free-flowing or pumpable and which may be incorporated in the products to be given a pearlescent appearance irrespective of their content of cationic or anionic components. In addition, it should be possible, if desired, to formulate these concentrates without alkanolamides and to provide the end product with the desired pearlescence, even with typical concentrations of pearlescing components therein.

SUMMARY OF THE INVENTION

It has now been found that all the requirements stated above are satisfied by a pearlescent concentrate in the form of a free-flowing, aqueous dispersion which is characterized by a content of (A) 15 to 40% by weight pearlescing components, (B) 5 to 55% by weight nonionic, ampholytic and/or zwitterionic emulsifiers and (C) 0.1 to 5% by weight low molecular weight, polyhydric alcohols.

DESCRIPTION OF PREFERRED EMBODIMENTS

Particularly advantageous properties are exhibited by pearlescent concentrates containing (A) 20 to 30% by weight pearlescing components, (B) 15 to 30% by weight nonionic, ampholytic and/or zwitterionic emulsifiers and (C) 0.5 to 3% by weight low molecular weight, polyhydric alcohols.

Pearlescing components are understood to be fusible fats or waxes which crystallize out in the form of fine, pearlescing substances on cooling of their aqueous solutions or emulsions in a temperature range of from about 30° to 90° C.

Preferred pearlescing components are (A1) esters corresponding to formula (I)

$$R^1 - (OC_nH_{2n})_x - OR^2 \qquad (I)$$

in which $R^1$ is a linear $C_{14-22}$ fatty acyl group, $R^2$ is hydrogen or a group $R^1$, n=2 or 3 and x is a number of from 1 to 4, (A2) monoalkanolamides corresponding to general formula (II)

$$R^3 - CO - NH - X \qquad (II)$$

in which $R^3$ is an alkyl group containing 8 to 22 and, more especially, 8 to 18 carbon atoms and X is a group $-CH_2-CH_2-OH$, a group $-CH_2-CH_2-CH_2-OH$ or a group $-C(CH_3)_2-OH$, (A3) linear, saturated $C_{16-22}$ fatty acids and (A4) β-ketosulfones corresponding to general formula (III)

$$R^4 - CO - CH(R^5) - SO_2 - CH_2 - R^6$$

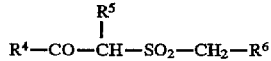

in which $R^4$ in which $C_{11-21}$ alkyl or alkenyl group, $R^5$ and $R^6$ are hydrogen atoms or together represent an ethylene group which forms a tetrahydrothiophene dioxide ring with the group between $R^5$ and $R^6$.

The pearlescent concentrates according to the invention may comprise exclusively representatives of one of these classes of compounds as well as mixtures of representatives of several of these classes of compounds.

Suitable esters (A1) corresponding to the general formula $R^1(OC_nH_{2n})_xOR^2$ are, for example, the monoesters and diesters of ethylene glycol and propylene glycol with higher fatty acids, for example with palmitic acid, stearic acid or behenic acid, or the diesters of diethylene glycol or triethylene glycol with such fatty acids. Also suitable are mixtures of monoesters and diesters of the glycols mentioned with fatty acid mixtures, for example with hydrogenated tallow fatty acid or with the saturated $C_{14-18}$ fatty acid fraction of tallow fatty acid. The ethylene glycol monoester and/or diester of palmitic and/or stearic acid is particularly suitable.

Preferred monoalkanolamides (A2) are the monoethanolamides. These compounds may contain individual alkyl radicals. However, it is standard practice to produce the alkanolamides of fatty acid mixtures from natural sources, for example coconut oil fatty acids, so that corresponding mixtures are present in regard to the alkyl radicals.

Suitable linear fatty acids (A3) are, for example, palmitic acid, stearic acid, arachic acid or behenic acid, although it is also possible to use technical fatty acid cuts consisting entirely or predominantly of $C_{16-22}$ fatty acids, for example palmitic/stearic acid fractions of the type obtained from tallow fatty acid by separation of the fatty acids liquid at +5° C. or palmitic/stearic acid fractions of the type obtainable by hydrogenation of tallow fatty acid.

The β-ketosulfones (A4) of general formula (III) have the advantage over the known ethylene glycol monoesters and diesters that the pearlescence of the preparations shows higher heat stability, i.e. the preparations retain their pearlescence for several hours on heating to temperatures above 50° C. and, in some cases, to temperatures above 70° C. Further information on the β-ketosulfones mentioned can be found in German patent application 35 08 051.

According to the invention, it is preferred to use the highly pearlescing compounds of classes (A1) and (A2).

Pearlescent concentrates in which at least 70% by weight and more especially at least 90% by weight of the pearlescing components consist of ethylene glycol distearate rate are particularly preferred.

Suitable emulsifiers (B) are nonionic, ampholytic and/or zwitterionic surface-active compounds distinguished by a lipophilic, preferably linear, alkyl or alkenyl group and at least one hydrophilic group. The hydrophilic group may be both an ionic group and also a nonionic group.

Nonionic emulsifiers contain, for example, a polyol group, a polyalkylene glycol ether group or a combination of a polyol group and a polyglycol ether group as the hydrophilic group.

Preferred pearlescent concentrates are those which contain as emulsifiers nonionic surfactants from the group consisting of (B1) adducts of 2 to 30 mol ethylene oxide and/or 0 to 5 mol propylene oxide with linear $C_{8-22}$ fatty alcohols, with $C_{12-22}$ fatty acids and with alkyl phenols containing 8 to 15 carbon atoms in the alkyl group, (B2) $C_{12-18}$ fatty acid monoesters and diesters of adducts of 1 to 30 mol ethylene oxide with glycerol, (B3) glycerol monoesters and diesters and sorbitan monoesters and diesters of saturated and unsaturated $C_{8-18}$ fatty acids and ethylene oxide adducts thereof, (B4) $C_{8-18}$ alkyl mono- and -oligoglycosides and ethoxylated analogs thereof and (B5) adducts of 10 to 60 mol ethylene oxide with castor oil and hydrogenated castor oil.

Mixtures of compounds from several of these classes are also suitable.

The adducts of ethylene oxide and/or propylene oxide with fatty alcohols, fatty acids, alkyl phenols, glycerol monoesters and diesters and sorbitan monoesters and diesters of fatty acids or with castor oil are known commercially available products. They are homolog mixtures of which the average degree of alkoxylation corresponds to the ratio between the quantities of ethylene oxide and/or propylene oxide and substrate with which the addition reaction is carried out.

$C_{12-18}$ fatty acid monoesters and diesters of adducts of ethylene oxide with glycerol are known from DE-PS 20 24 051 as oil-restoring agents for cosmetic preparations. $C_{8-18}$ mono- and oligo-glycosides, their production and their use as surfactants are known, for example, from U.S. Pat. No. 3,839,318, U.S. Pat. No. 3,707,535, U.S. Pat. No. 3,547,828, DE-A 19 43 689, DE-A 20 36 472 and DE-A 30 01 064 and from EP-A 77 167. They are prepared in particular by reaction of glucose or oligo-saccharides with primary $C_{8-18}$ s alcohols. So far as the glycoside residue is concerned, both monoglycosides, in which a cyclic sugar residue is attached to the fatty alcohol by a glycoside bond, and also oligomeric glycosides having a degree of oligomerization of up to, preferably, 8 are suitable. The degree of oligomerization is a statistical mean value on which a homolog distribution typical of such technical products is based.

The compounds of group (B1) are particularly preferred nonionic emulsifiers (B) for the purposes of the invention.

Zwitterionic surfactants may also be used as the emulsifiers (B). Zwitterionic surfactants are surface-active compounds which contain at least one quaternary ammonium group and at least one $—COO^{(-)}$ or $—SO_3^{(-)}$ group in the molecule. Particularly suitable zwitterionic surfactants are the so-called betaines, such as the N-alkyl-N,N'-dimethyl ammonium glycinates, for example coconut alkyl dimethyl ammonium glycinate, N-acylaminopropyl-N,N-dimethyl ammonium glycinates, for example coconut acylaminopropyl dimethyl ammonium glycinate, and 2-alkyl-3-carboxymethyl-3-hydroxyethyl imidazolines containing 8 to 18carbon atoms in the alkyl or acyl group and also coconut acylaminoethyl hydroxyethyl carboxymethyl glycinate. The fatty acid amide derivative known by the CTFA name of cocoamidopropyl betaine is particularly preferred.

Other suitable emulsifiers (B) are ampholytic surfactants. Ampholytic surfactants are surface-active compounds which, in addition to a $C_{8-18}$ is alkyl or acyl group in the molecule, contain at least one free amino group and at least one —COOH or —SO$_3$H group and are capable of forming inner salts. Examples of suitable ampholytic surfactants are N-alkyl glycines, N-alkylpropionic acids, N-alkylaminobutyric acids, N-alkyliminodipropionic acids, N-hydroxyethyl-N-alkylamidopropyl glycines, N-alkyltaurines, N-alkylsarcosines, 2-alkylaminopropionic acids and alkylaminoacetic acids containing approximately 8 to 18 carbon atoms in the alkyl group. Particularly preferred ampholytic surfactants are N-coconut alkylaminopropionate, coconut acylaminoethylamine propionate and $C_{12-18}$ sarcosine.

According to the invention, the pearlescent concentrates may contain representatives of one or more of the above-mentioned classes of surfactants. Where mixtures are used, it is preferred to use nonionic and zwitterionic and/or ampholytic surfactants in a ratio by weight of 5:1 to 1:5.

The pearlescent concentrates according to the invention, which contain only nonionic, zwitterionic and/or ampholytic surfactants, have proved to be particularly universally usable and to be particularly compatible with aqueous preparations of water-soluble surfactants of any type and any ionicity.

If desired, however, the pearlescent concentrates may also contain anionic or cationic emulsifiers.

Suitable anionic emulsifiers are, for example, alkyl sulfates and alkyl polyethylene glycol ether sulfates containing 1 to 6 ethylene glycol ether groups in the molecule which are used in the form of their alkali, magnesium, ammonium, mono-, di- or trialkanolammonium salts containing 2 to 3 carbon atoms in the alkanol group. Other suitable anionic surfactants are alkanesulfonates, α-olefin sulfonates, α-sulfofatty acid methyl esters, fatty alcohol (polyglycol ether) carboxylates, sulfosuccinic acid mono- and dialkyl esters, sulfosuccinic acid ester salts, acyl isethionates, acyl taurides and acyl sarcosides. Soaps may also be used as emulsifiers. This may be achieved, for example, by saponifying a small proportion, for example 1 to 20% by weight, of the linear, saturated fatty acids by added alkali hydroxide and thus converting it into an anionic emulsifier. Preferred anionic surfactants are the alkyl polyethylene glycol ether sulfates such as, for example, sodium lauryl polyglycol ether sulfate.

Suitable cationic emulsifiers are quaternary ammonium surfactants, for example alkyl trimethyl ammonium chlorides and dialkyl dimethyl ammonium chlorides, for example cetyl trimethyl ammonium chloride, stearyl trimethyl ammonium chloride, distearyl dimethyl ammonium chloride, lauryl dimethyl ammonium chloride and lauryl dimethyl benzyl ammonium chloride, cetyl pyridinium chloride and tallow alkyl tris-(oligooxyalkyl)-ammonium phosphate.

The alkyl groups in the anionic and cationic surfactants mentioned typically contain 8 to 22 and more especially 12 to 18 carbon atoms.

The compounds containing alkyl groups used as surfactants may be individual substances. However, it is generally preferred to use native vegetable and animal starting materials in the production of these compounds, so that mixtures having different alkyl chain lengths depending on the particular starting material used are obtained.

The content of low molecular weight polyhydric alcohols is crucial to the flowability or pumpability of the pearlescent concentrates according to the invention. Preferred low molecular weight polyhydric alcohols contain 2 to 6 carbon atoms and 2 to 6 hydroxyl groups. Alcohols such as these are, for example, ethylene glycol, 1,2- and 1,3-propylene glycol, glycerol, di- and triethylene glycol, erythritol, arabitol, adonitol, xylitol, sorbitol, mannitol and galactitol. It is particularly preferred to use compounds which are liquid at room temperature, particularly 1,2-propylene glycol and/or glycerol.

In the case of pearlescent concentrates containing less than about 30% by weight pearlescing components, a content of low molecular weight polyhydric alcohols of approximately 1% by weight has proved to be sufficient in many cases. This applies above all when 1,2-propylene glycol and/or glycerol is used as the alcohol component.

In addition to the components mentioned above, the pearlescent concentrates according to the invention essentially contain water. Commercially available preservatives may be added in small quantities to protect the concentrates against bacterial and fungal attack. In addition, the concentrates may contain small quantities of buffers to adjust the pH to values in the range from 2 to 8, for example citric acid and/or sodium citrate.

The pearlescent concentrates according to the invention are pumpable at least over a temperature range of 5° to 40° C. and remain stable in storage for prolonged periods, i.e. for at least about 3 months.

The pearlescent concentrates according to the invention are preferably prepared by initially heating components (A), (B) and (C) together to a temperature approximately 1° to 30° C. above the melting point. In most cases, this will be a temperature in the range from about 60° to 90° C. The water heated to substantially the same temperature is then added to this mixture. Where an ionic water-soluble surfactant is used as the emulsifier, it may be preferred to dissolve it in the aqueous phase and to introduce it together with the water into the mixture. The aqueous phase may even already contain the buffer substances in dissolved form. The dispersion formed is then cooled with continuous stirring to room temperature, i.e. to around 25° C. In most cases, the viscosity of the pearlescent concentrate is so low that there is no need to use special stirring units, such as homogenizers or other high-speed mixers. Temperature-sensitive preservatives should only be added after cooling to temperatures below 40° C. and, in particular, only just before the end of the cooling phase at temperatures of the order of 30° C.

The pearlescent concentrates according to the invention are suitable for the production of clouded and pearlescent, liquid aqueous preparations of water-soluble surfactants. They may be incorporated, for example, in liquid detergents, such as dishwashing detergents, liquid light-duty detergents and liquid soaps but are preferably incorporated in liquid personal hygiene and body-care preparations, such as for example shampoos, liquid hand and body soaps, shower bath preparations, bath additives (bubble baths), hair rinses or hair dyes.

To produce pearlescence, the pearlescent concentrates according to the invention are added to the clear aqueous preparations at 0° to 40° C. in a quantity of 1 to 10% by weight and more especially in a quantity of 1.5 to 5% by weight of the preparation and are dispersed therein with stirring. A metallic, dense to slightly glossy, extremely dense pearlescence is obtained, depending on the preparation and the concentration used.

The following Examples are intended to illustrate the invention without limiting it in any way.

EXAMPLES

Free-flowing pearlescent concentrates having the compositions shown in Table 1 were prepared. Where dilute solutions of components (A) and (B) were used, the quantities are based on % by weight of active substance. The substances shown in the form of trade names are the following substances:

1 ethylene glycol distearate (at least 90% diester) (HENKEL)

2 coconut oil fatty acid monoethanolamide (approx. 95% amide) (HENKEL)

composition of the fatty acid:
        approx. 56% lauric acid
        approx. 21% myristic acid
        approx. 10% palmitic acid
        approx. 13% stearic acid and oleic acid 3 $C_{12-14}$ fatty alcohol +4 ethylene oxide (HENKEL) aqueous solution of a fatty acid amide derivative of betaine structure having the formula

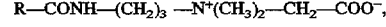

$$R-CONH-(CH_2)_3-N^+(CH_3)_2-CH_2-COO^-,$$

CTFA name cocamidopropyl betaine (approx. 30% active substance, approx. 5% NaCl) (HENKEL)

5 $C_{12-14}$ fatty alcohol +3 ethylene oxide (HENKEL)

6 86% Water

The quantities of components A, B and C used were heated to a temperature of 75° C. The water heated to 75° C. was added to this melt. The dispersion was then cooled with continuous stirring to 25° C., the preservative being added at a temperature of 30° C.

TABLE I

Free-flowing pearlescent concentrates

| Components | \multicolumn{12}{c}{Content (% by weight) Mixture No.} |
|---|---|

| Components | 1 | 2 | 3 | 4 | 5 | 6 | 7 | 8 | 9 | 10 | 11 | 12 |
|---|---|---|---|---|---|---|---|---|---|---|---|---|
| Pearlescer (A) | 25 | 25 | 25 | 30 | 30 | 30 | 25 | 25 | 25 | 25 | 25 | 25 |
| including |  |  |  |  |  |  |  |  |  |  |  |  |
| Cutina® AGS¹ | 25 | 25 | 25 | 30 | 30 | 25 | 25 | 25 | 25 | 25 | 25 | 25 |
| Comperlan® 100² | — | — | — | — | — | 5 | — | — | — | — | — | — |
| Emulsifier (B) | 19 | 17 | 19 | 20.5 | 20.5 | 20.5 | 17 | 18 | 17 | 17 | 19 | 18.5 |
| including |  |  |  |  |  |  |  |  |  |  |  |  |
| Dehydol® LS4³ | 5 | 11 | 5 | 13 | 13 | 13 | 11 | 8 | 11 | 11 | 5 | 11 |
| Dehyton® K⁴ | 9 | 6 | 9 | 7.5 | 7.5 | 7.5 | 6 | 6 | 6 | 6 | 9 | 7.5 |
| Dehydol® LS3⁵ | 5 | — | 5 | — | — | — | — | 4 | — | — | 5 | — |
| Alcohol (C) | 1 | 5 | 1 | 5 | 5 | 5 | 5 | 1 | 1 | 1 | 1 | 5 |
| including |  |  |  |  |  |  |  |  |  |  |  |  |
| glycerol⁶ | — | 5 | 1 | 5 | — | 5 | — | — | 1 | — | 1 | 3 |
| 1,2-propylene glycol | 1 | — | — | — | 5 | — | 5 | 1 | — | 1 | — | 2 |
| Water |  |  |  |  |  |  |  |  |  |  |  |  |
| Preservative | \multicolumn{12}{c}{ad 100} |
| Buffer |  |  |  |  |  |  |  |  |  |  |  |  |

The viscosites of the pearlescent concentrates were measured with a Brookfield RVF Viscosimeter, spindle 5, 10 revolutions per minute, at the particular temperature at which the mixture had been stored. Except for the absence of component C, the comparison mixture Cx had the same composition as the mixture x. The measured values are shown in Table 2.

TABLE 2

Viscosity Values

| Mixture No. | Temperature [°C.] | Storage time [days] | Viscosity [mPa · s] |
|---|---|---|---|
| 2 | 10 | 1 | 14400 |
| 2 | 25 | 1 | 6000 |
| 2 | 40 | 1 | 14000 |
| 7 | 10 | 1 | 14000 |
| 7 | 25 | 1 | 5600 |
| 7 | 40 | 1 | 8000 |
| 9 | 10 | 14 | 14000 |
| C9 | 10 | 14 | 22000 |
| 9 | 25 | 1 | 6000 |
| C9 | 25 | 1 | 11200 |
| 9 | 25 | 7 | 5200 |
| C9 | 25 | 7 | 12000 |
| 9 | 25 | 14 | 5200 |
| C9 | 25 | 14 | 12000 |
| 9 | 40 | 14 | 14000 |
| C9 | 40 | 14 | 20000 |
| 10 | 10 | 14 | 16000 |
| C10 | 10 | 14 | 22000 |
| 10 | 25 | 1 | 6000 |
| C10 | 25 | 1 | 11200 |
| 10 | 25 | 7 | 6000 |
| C10 | 25 | 7 | 12000 |
| 10 | 25 | 14 | 6400 |
| C10 | 25 | 14 | 12000 |
| 10 | 40 | 14 | 13600 |
| C10 | 40 | 14 | 20000 |

The results show the distinct reduction in viscosity by the addition of alcohol.

Application Examples

1) Shampoo containing anionic surfactants

| Component | % by weight |
|---|---|
| Fatty alcohol (C₁₂₋₁₄) polyglycol (2 EO) ether sulfate, sodium salt, approx. 30% in water (CTFA name: sodium laureth sulfate) | 40.0 |
| N-coconut acylamidopropyl dimethyl glycine, 30% in water (CTFA name: cocamidopropyl betaine) | 10.0 |
| Cetiol$^{(R)}$ HE⁷ | 2.0 |
| Pearlescent concentrate mixture 9 | 3.0 |
| Sodium chloride | 0.8 |
| Water | ad 100 |

2) Foam bath containing anionic surfactants

| | |
|---|---|
| Fatty alcohol (C₁₂₋₁₄) sulfate magnesium salt, approx. 30% in water (CTFA name: Magnesium lauryl sulfate) | 40.0 |
| N-coconut acylamidopropyl dimethyl glycine, 30% in water (CTFA name: cocamidopropyl betaine) | 10.0 |
| Sulfosuccinic acid monolauryl polyglycol (3 EO) ester, 40% in water (CTFA name: disodium laureth sulfosuccinate) | 4.5 |
| Cetiol$^{(R)}$ HE⁷ | 2.0 |
| Pearlescent concentrate mixture 7 | 3.0 |
| Sodium chloride | 0.3 |
| Water | ad 100 |

3) Hair treatment containing cationic surfactants

| | |
|---|---|
| Quaternum 52⁸ | 2.0 |
| Cetiol$^{(R)}$ HE | 0.5 |
| Viscontran$^{(R)}$ HEC 30000 PR⁹ | 50.0 |
| Pearlescent concentrate mixture 2 | 5.0 |
| Citric acid | 0.2 |
| Water | ad 100 |

⁷Polyol fatty acid ester (CTFA name: PEG-7-Glyceryl Cocoate) (HENKEL)
⁸Tris-(oligooxyethyl)-alkyl ammonium phosphate, 50% in water (HENKEL)
⁹Hydroxyethyl cellulose, 2% in water (AQUALON)

What is claimed is:
1. A peadescent free-flowing, aqueous concentrate consisting essentially of:

(A) 20% to 30% by weight of pearlescing components consisting of esters corresponding to formula (I)

$$R^1-(OC_nH_{2n})_x-OR^2 \qquad (I)$$

in which $R^1$ is a linear $C_{14-22}$ fatty acyl group. $R^2$ is hydrogen or a group $R^1$, n=2 or 3 and x is a number of from 1 to 4.

(B) 15% to 30% by weight of a component selected from the group of nonionic, ampholytic, and zwitterionic emulsifiers and mixtures thereof, (C) 0.1% to 5% by weight of low molecular weight, polyhydric alcohols and (D) the remainder, water, based on the weight of said dispersion.

2. A pearlescent concentrate as claimed in claim 1 wherein at least 70% by weight of the pearlescing components consist of ethylene glycol distearate.

3. A pearlescent concentrate as claimed in claim 1, wherein said component (B) is selected from the group consisting of (B1) adducts of 2 to 30 mol ethylene oxide and 0 to 5 mol propylene oxide with linear $C_{8-14,22}$ fatty alcohols, with $C_{12-22}$ fatty acids and with alkyl phenols containing 8 to 15 carbon atoms in the alkyl group, (B2) $C_{2-18}$ fatty acid monoesters and diesters of adducts of 1 to 30 mol ethylene oxide with glycerol, (B3) glycerol monoesters and diesters and sorbitan monoesters and diesters of saturated and unsaturated $C_{8-18}$ fatty acids and ethylene oxide adducts thereof, (B4) $C_{8-18}$ alkyl mono- and oligo-glycosides and ethoxylated analogs thereof, and (B5) adducts of 10 to 60 mol ethylene oxide with castor oil and hydrogenated castor oil.

4. A pearlescent concentrate as claimed in claim 1, wherein said component (B) consists of a first surfactant component selected from the group consisting of nonionic suffactants and a second surfactant component selected from the group consisting of zwitterionic suffactants, ampholytic surfactants, and mixtures thereof, said first and second surfactant components being present in a ratio by weight of 5:1 to 1:5.

5. A pearlescent concentrate as claimed in claim 1, wherein the low molecular weight polyhydric alcohol component is selected from the group consisting of alcohol molecules containing 2 to 6 carbon atoms and 2 to 6 hydroxyl groups each.

6. A pearlescent concentrate as claimed in claim 5 wherein the low molecular weight polyhydric alcohol component is selected from the group consisting of 1,2-propylene glycol, glycerol, and mixtures thereof.

7. A pearlescent concentrate as claimed in claim 1 wherein at least 90% by weight of the pearlescing components consist of ethylene glycol distearate.

8. A pearlescent concentrate as claimed in claim 1 wherein said zwitterionic emulsifiers are betaines.

9. A process for the production of pearlescent concentrates, wherein a mixture consisting essentially of:

(A) pearlescing components consisting of esters corresponding to formula (I)

$$R^1-(OC_nH_{2n})_x-OR^2 \qquad (I)$$

in which $R^1$ is a linear $C_{14-22}$ fatty acyl group, $R^2$ is hydrogen or a group $R^1$, n=2 or 3 and x is a number of from 1 to 4.

(B) a component selected from the group of nonionic, ampholytic, and zwitterionic emulsifiers and mixtures thereof, and (C) a component of low molecular weight, polyhydric alcohols is heated to a temperature 1° C. to 30° C. above the melting point of the mixture, mixed with a quantity of water at substantially the same temperature, and the resulting mixture is subsequently cooled to room temperature, the quantities of water and of components (A), (B), and (C) used being such that the resulting concentrate contains from 20% to 30% by weight of component (A), from 15% to 30% by weight of component (B), from 0.1% to 5% by weight of component (C) and the remainder, water.

10. A process for the production of clouded and pearlescent free-flowing, aqueous preparations of water-soluble surfactants, wherein a pearlescent concentrate consisting essentially of:

(A) 20% to 30% by weight of pearlescing components consisting of esters corresponding to formula (I)

$$R^1-(OC_nH_{2n})_x-OR^2 \qquad (I)$$

in which $R^1$ is a linear $C_{14-22}$ fatty acyl group, $R^2$ is hydrogen or a group $R^1$, n=2 or 3 and x is a number of from 1 to 4.

(B) 15% to 30% by weight of a component selected from the group of nonionic, ampholytic, and zwitterionic emulsifiers and mixtures thereof, and (C) 0.1% to 5% by weight of low molecular weight, polyhydric alcohols, and optionally, water is added to the clear aqueous preparations at a temperature of from 0° C. to 40° C. in a quantity of from 0.5% to 10% by weight and is dispersed therein with stirring.

* * * * *